United States Patent [19]

Moritz

[11] 4,417,701
[45] Nov. 29, 1983

[54] METHOD AND MEANS FOR CONTROLLING THE MANUFACTURE OF WINDINGS FOR INDUCTIVE APPARATUS

[75] Inventor: Bertil Moritz, Ludvika, Sweden

[73] Assignee: ASEA Aktiebolag, Västerås, Sweden

[21] Appl. No.: 349,655

[22] Filed: Feb. 17, 1982

[30] Foreign Application Priority Data

Feb. 19, 1981 [SE] Sweden .............................. 8101112

[51] Int. Cl.³ ...................... B65H 39/16; H01G 7/00
[52] U.S. Cl. .................................... 242/55; 29/25.42; 242/56.1; 324/54
[58] Field of Search .................. 242/56 R, 56.1, 56.2, 242/56.4, 56.5, 55; 29/730, 731, 25.41, 25.42; 324/51, 54, 111, 60 R, 60 C, 60 CD, 61

[56] References Cited

U.S. PATENT DOCUMENTS

| | | | |
|---|---|---|---|
| Re. 30,775 | 10/1981 | Miller et al. | 29/25.42 |
| 2,942,248 | 6/1960 | Huggins | 324/54 X |
| 3,355,664 | 11/1967 | Pranke | 324/61 |
| 3,407,465 | 10/1968 | Ortel | 29/25.42 |
| 4,276,683 | 7/1981 | Konno et al. | 29/25.42 |

Primary Examiner—Leonard D. Christian
Attorney, Agent, or Firm—Watson, Cole, Grindle & Watson

[57] ABSTRACT

A method of, and means for, controlling the manufacture of a winding for an inductive apparatus, for example a transformer winding or a reactor winding, which winding is of the kind comprising a plurality of turns of a sheet composed of an electrically conductive metallic foil and an electrically insulating film on each side of the metallic foil. During the winding of the sheet, the metallic foil together with the insulating films is passed through at least one electrode device which comprises at least two rolls arranged one on each side of the sheet and having a different voltage compared with the metallic foil. At the electrode device, the insulating films are pressed with a certain pressure against the metallic foil across the entire width of the latter by means of the rolls, and the electrical insulation of both sides of the sheet is checked by separately sensing the leakage current which via each of the rolls passes through the respective insulating film.

10 Claims, 5 Drawing Figures

METHOD AND MEANS FOR CONTROLLING THE MANUFACTURE OF WINDINGS FOR INDUCTIVE APPARATUS

TECHNICAL FIELD

This invention relates to a method of, and means for, controlling the manufacture of a winding of an inductive apparatus, for example a transformer winding or a reactor winding, which winding is of the kind comprising a plurality of turns of a sheet composed of an electrically conductive metallic foil and an electrically insulating film on each side of said metallic foil. For the sake of simplicity in the ensuing description, such windings will be referred to as sheet windings.

In the manufacture of a sheet winding in a workshop environment, it is impossible in practice to prevent small metallic particles, for example small particles of iron, copper and aluminum, entering the winding from the surroundings. Such particles, which frequently occur in a workshop environment, often have sharp edges and therefore they may damage the insulating films, and if they are sufficiently large they may cut through the insulating films so that a short-circuit between turns of the conductive metallic foil may arise instantaneously or after a certain time of operation of the winding. Since such damage may be caused by very small particles, for example of an order of size corresponding to the thickness of the insulating films (which may be considerably below 0.1 mm), it is very difficult in practice or would in any case require the installation of extremely costly cleaning plant to prevent the winding from being damaged by metallic particles. A turn short-circuit may also occur as a result of burrs on the conductive metallic foil or defects in the insulating films.

In view of the fact that a sheet winding for a large power transformer represents substantial costs in material and work, it is hardly defensible from an economic point of view, having regard to the above-mentioned risks of insulation damage during manufacture, to wait until the manufacture of a winding is finished before it is voltage-tested.

BACKGROUND ART

It is previously known to voltage-test an electrically insulating film by passing it between two rolls which are under voltage with respect to each other and which are urged with a certain force towards each other (see German Offenlegungsschrift No. 2438094). However, when it is a question of an insulated metallic foil for a sheet winding, it is not sufficient only to test the insulating films, since an insulating film which is perfect per se may become damaged during the winding process by particles or burrs on the metallic foil cutting through the insulating films.

The present invention aims to provide a method of, and means for, controlling the manufacture of a sheet winding of the kind referred to, in which insulation faults, if any, may be detected and be repaired at the time of winding. The invention also aims to provide such a method, or means, which can be employed with relatively wide conductive metallic foils without the uncertainty factors associated with prior art methods.

DISCLOSURE OF THE INVENTION

According to one aspect of the invention, a method of controlling the manufacture of a winding for an inductive apparatus, which winding is of the kind comprising a plurality of turns of a sheet composed of an electrically conductive metallic foil and an electrically insulating film on each side of said metallic foil, comprises the steps, effected during the winding process, of passing said metallic foil together with said insulating films through at least one electrode device comprising at least two rolls arranged one on each side of said sheet and having a different voltage compared with said foil, pressing said insulating films with a certain pressure against said metallic foil across the entire width of said foil by means of said rolls, and checking the electrical insulation of both sides of said sheet by separately sensing the leakage current which via each of said rolls passes through the respective insulating film.

In the method in accordance with the invention it is important that the insulation of the metallic foil is provided by an insulating film on each side of the foil, since in this way both sides of the foil, as well as the insulating films, can be tested separately. Preferably, the conductive metallic foil is grounded and voltage is applied to each of said rolls.

The voltage testing is suitably carried out using direct voltage, since in that case the stationary leakage currents through the insulating films are negligible in relation to the current which appears in the event of a fault in the insulation of the sheet. Such a fault can therefore be detected more easily than if the testing were carried out using alternating voltage. Again, because of the relatively large capacitance between a respective roll under voltage and the conductive foil, a relatively large stationary displacement current will flow in the test circuit if alternating voltage is used for the testing, which renders the fault detection more difficult.

To bring about an even pressure across the entire width of the sheet at the electrode device, one of the rolls of the latter may be very flexible and have a considerably smaller diameter than the other roll, which in its turn functions as a supporting roll for the flexible roll. Both the flexible roll and the supporting roll have relatively hard surfaces and the flexible roll may be pressed against the sheet by a plurality of coaxially arranged, short supporting rollers. Another possibility is to use two separate roll pairs for testing both sides of the sheet, in which case the roll which is under voltage in each roll pair may be made of metallic material, for example steel, whereas the other roll may be made of, or comprise a layer of, electrically insulating, elastomeric material, for example rubber or the like.

The conductive metallic foil used in the manufacture of a winding of the kind with which this invention is concerned may be an aluminum foil having a thickness preferably of from about 0.05 mm to about 3 mm. The insulating films may with advantage consist of polymer films, suitable polymers being polyethylene glycol terephthalate, cellulose acetate, a polycarbonate, a polyimide or a polyamide.

According to a further aspect of the invention, means for carrying out the method in accordance with the invention comprises at least one electrode device having at least two rolls arranged one on each side of said sheet, means pressing at least one of said rolls against said sheet with a certain pressure across the entire width of said sheet, a voltage source for establishing a voltage difference between said rolls and said conductive metallic foil, members for sensing a leakage current, if any, which via each of said rolls passes through the respective insulating film, and members for temporarily interrupting the winding process to enable strengthening of the insulation if the leakage current exceeds a predetermined value.

BRIEF DESCRIPTION OF THE DRAWINGS

The invention will now be described, by way of example, with reference to the accompanying drawings, in which.

DESCRIPTION OF PREFERRED EMBODIMENTS

Figure 1:
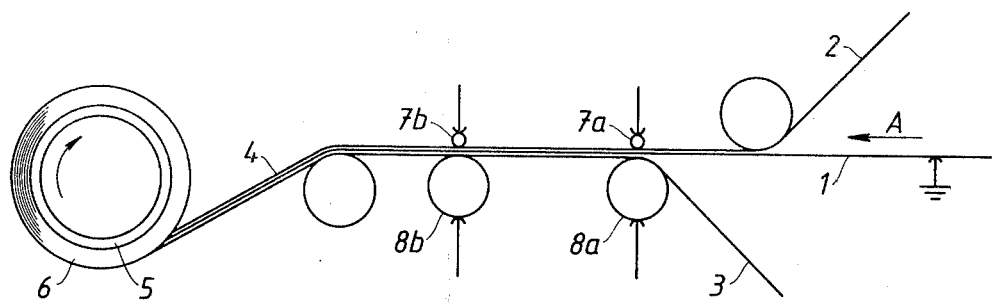
FIG. 1 is a schematic side view of one embodiment of means for carrying out the method in accordance with the invention.

FIG. 1 shows a conductive metallic foil 1, for example of aluminum or copper, proceeding from a storage roll (not shown) in the direction of the arrow A, which foil is being coated with electrically insulating films 2, 3, one on each side of the foil 1. The insulating films 2,3 may possibly be secured to the foil 1, for example by glueing, but they may be applied to the foil without employing an intermediate binder. The conductive foil with the insulating films forms an electrically insulated sheet 4 which is wound up on a supporting cylinder 5 to form a sheet winding 6, which is intended to constitute the winding of a transformer. The metallic foil 1 may have a thickness of, for example, about 0.5 mm and a width of, for example, about 1.5 m. The insulating films 2, 3 may have a thickness of, for example, about 0.05 mm and should be somewhat wider than the metallic foil 1 so as to extend outside the edges of the metallic foil, thus preventing electrical flash-overs along the edges of the winding.

During the winding process the conductive foil 1 is grounded, and, after the insulating films 2, 3 have been applied, the sheet 4 is conducted through two electrode devices which are under voltage and are arranged in spaced-apart relationship along the path of travel of the sheet 4. These electrode devices each comprise two rolls 7a, 8a and 7b, 8b, respectively, the rolls of each pair being arranged on opposite sides of the sheet 4. One roll 7a and 7b, respectively, in each roll pair is very flexible, and it is influenced by a device, which will be described hereinafter in greater detail with reference to FIGS. 3 and 4, in such a way that it will make contact with the sheet 4 with a pressure which is uniform across the entire width of the sheet. The other roll 8a and 8b, respectively, in each roll pair has a considerably larger diameter than the flexible roll and acts as a supporting roll. The diameter of each of the flexible rolls 7a, 7b may be, for example, about 10 mm, whereas the diameter of each of the supporting rolls 8a, 8b may be, for example, about 200 mm. Both the rolls in each roll pair have a relatively hard surface.

When the insulated sheet 4 is passed through the first electrode device 7a, 8a, the insulating capacity of the films 2, 3 is checked by sensing the leakage current which, via each of the rolls 7a, 8a, passes through the respective insulating film. If a fault reduces the insulating capacity at a point on either side of the sheet 4, a relay (not shown) is arranged to arrest the forward motion of the sheet 4 in such a way that the fault point will be located in the region between the two electrode devices at a predetermined distance from the roll pair 7a, 8a. When the sheet 4 has been brought to rest, a strip of insulating film, which extends across the entire width of the sheet 4, is applied to that side of the sheet 4 where the fault has been detected. Thus, the fault does not have to be seen, and the application of the strip of insulating film may be effected entirely automatically. Thereafter, the winding process continues, and a renewed voltage testing is carried out at the roll pair 7b, 8b. Thus, with this arrangement it is not necessary to reverse the direction of travel of the sheet 4 in order to repair an insulation fault.

Figure 2:
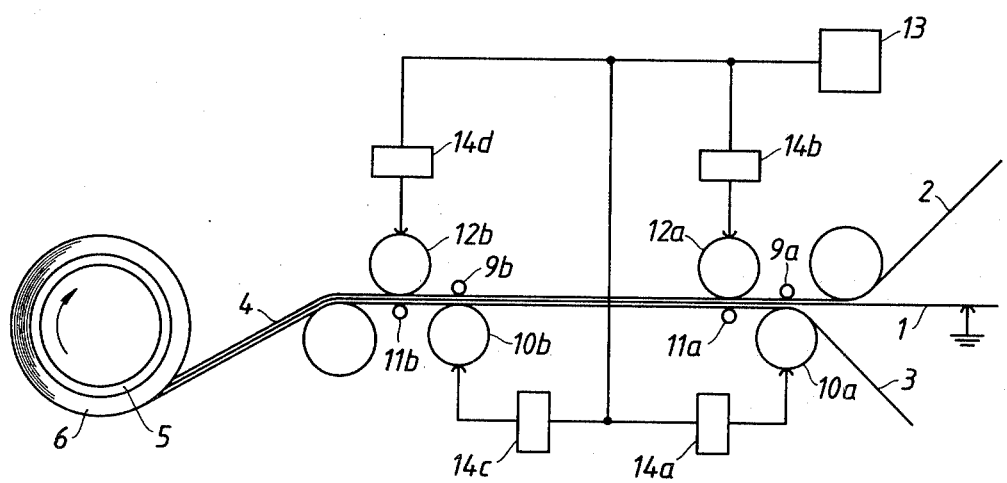
FIG. 2 is a view similar to FIG. 1 of a modified embodiment of means for carrying out the method in accordance with the invention.

The two rolls in each roll pair are suitably given the same potential but should be connected to separate current sensing members, since it is desired to be able to determine directly on which side of the sheet 4 a possible insulation fault is located. However, with the embodiment according to FIG. 1 it may be difficult to make this determination with certainty, since metallic contact may easily occur between the rolls at their end portions. This is due to the rolls normally being longer than the width of the sheet 4 and to the sheet having a small thickness. This drawback is avoided by the embodiment according to FIG. 2, in which each electrode device comprises two roll pairs 9a, 10a; 11a, 12a and 9b, 10b; 11b, 12b, respectively, in which only one roll 10a, 12a and 10b, 12b, respectively, in each roll pair is subjected to voltage, whereas the other roll 9a, 11a and 9b, 11b, respectively, in an insulated roll. FIG. 2 also shows a test voltage generator 13 and current sensing members 14a–14d. The voltage connection to the different rolls takes place via spring-loaded carbon brushes.

Figure 3:
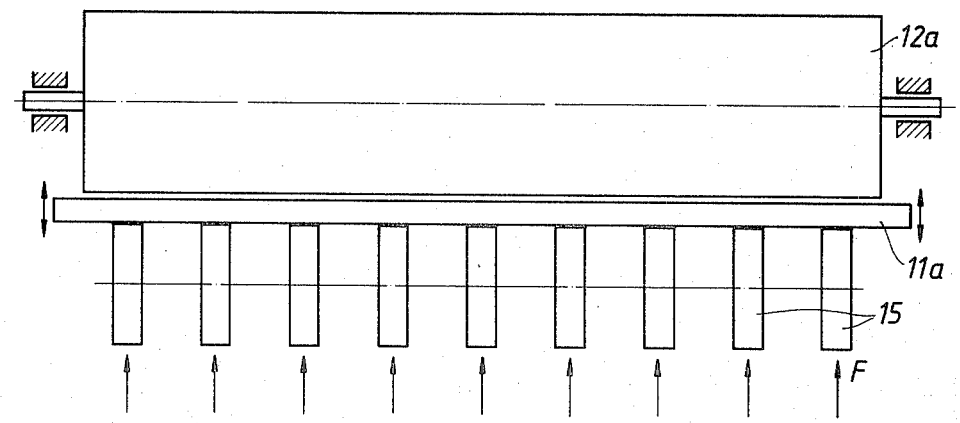
FIG. 3 is an end view, on an enlarged scale, of a roll pair forming part of the means of FIG. 1 or 2.
Figure 4:
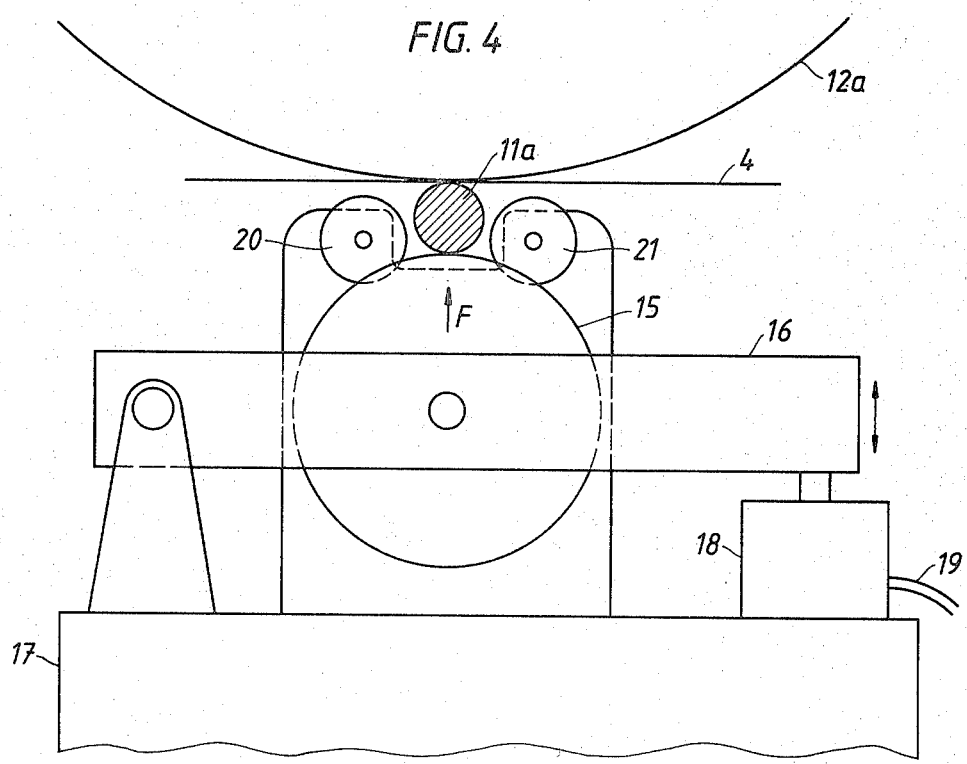
FIG. 4 is a sectional side view, on an enlarged scale, corresponding to FIG. 3.

FIGS. 3 and 4 show one possible embodiment of a roll pair for use in the means of FIG. 1 or FIG. 2 for achieving a uniform pressure across the width of the sheet 4, the two rolls of the roll pair being designated by the numerals 11a and 12a, respectively. In the roll pair shown in FIGS. 3 and 4, a large number of coaxially arranged rollers 15, for example thirty such rollers, are evenly distributed along the roll 11a. Each roller 15 is journalled on an arm 16 (FIG. 4) which at one end is pivotally mounted on a stand 17 and at the other end is connected to a pneumatic cylinder 18. Compressed air supplied to the cylinders 18 via respective conduits 19 results in each of the rollers 15 being pressed with a force F against the flexible roll 11a, which will then make contact with the sheet 4 with a pressure which is substantially uniform across the entire width of the sheet 4. The roll 11a is held in position by pairs of supporting rollers 20, 21, journalled on the stand 17, the rollers of each pair being diametrically arranged with respect to their associated roller 15. In principle, the roll 11a need not be journalled at its ends. However, it may be practical to provide the roll 11a with such support, which, however, is designed in such a way that radial movement of the roll 11a towards the supporting roll 12a is not prevented.

Figure 5:
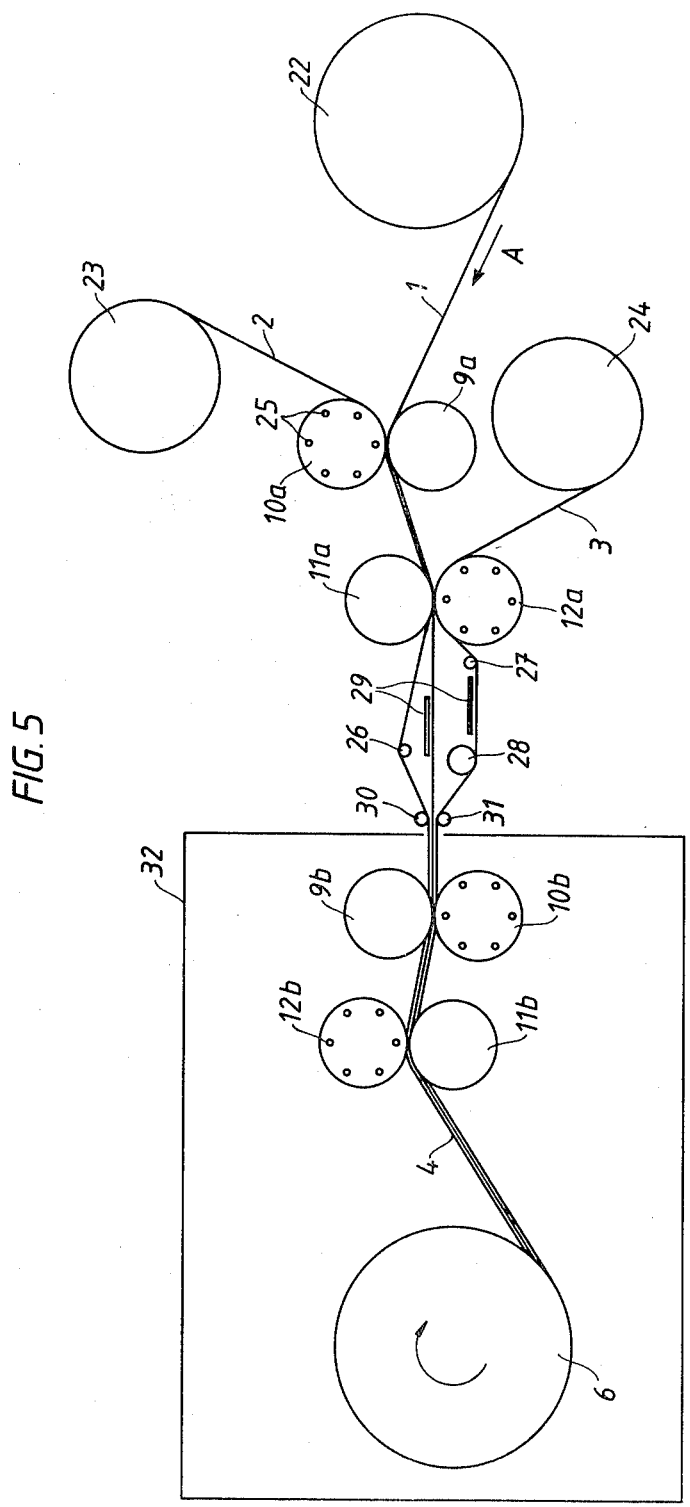
FIG. 5 is a schematic side view of a further embodiment of means for carrying out the method in accordance with the invention.

In the embodiment shown in FIG. 5, a metallic foil 1 proceeds in the direction of the arrow A from a storage roller 22, and two electrically insulating films 2, 3 proceed from storage rollers 23 and 24, respectively, towards the foil 1 on opposite sides of the latter. In a first control station comprising two roll pairs 9a, 10a and 11a, 12a, respectively, the insulating films 2, 3 are voltage-tested separately while being pressed with a certain force against the surfaces of the metallic foil 1. One roll 10a and 12a, respectively, in each roll pair is, at least as regards its envelope surface, made of metallic material, for example steel, and constitutes one of the electrodes during voltage testing, whereas the metallic foil 1 constitutes the other electrode. The other roll 9a and 11a, respectively, in each roll pair is, at least in a layer nearest its envelope surface, made of an electrically insulating, elastomeric material, for example rubber, whereby an approximately uniform pressure distribution across the entire width of the sheet 4 can be obtained.

Inside the rolls 10a and 12a, which are under voltage, there are arranged electric heating elements 25, rotatable with the rolls, which keep the rolls hot. In this way, the films 2, 3 and the foil 1 are subjected not only to pressure and voltage during passage through the roll pairs, but also to heating.

After passing through the roll pair 11a, 12a, the insulating films 2, 3 are moved away from the metallic foil 1 with the help of deflector rollers 26, 27 and 28. This makes it possible to insert repair strips 29 of insulating film between the films 2, 3 and the foil 1 when a possible insulation fault has been indicated on either side of the foil 1. Because the repair strips 29 are inserted from the side and are held in position by the film 2 or 3, other objects are prevented from entering between the films and the foil and there will be no problems with attachment of the strips.

After a possible repair, the insulating films 2, 3 and the foil 1 are brought together again by means of a roller pair 30, 31, after which the films and the foil enter into an enclosed clean space 32. In order to check that no contamination of the films 2, 3 or the foil 1 has occurred after the first testing, the test is repeated in the same way at a second control station, which is accommodated in the enclosed space 32 and which, in the same way as the first control station, comprises two roll pairs 9b, 10b and 11b, 12b. If an insulation fault is indicated here, the winding machine is reversed and repair is performed outside the clean space 32 at a location in the machine provided for this purpose.

What is claimed is:

1. A method of controlling the manufacture of a winding for an inductive apparatus, which winding is of the kind comprising a plurality of turns of a sheet composed of an electrically conductive metallic foil and an electrically insulating film on each side of said metallic foil, said method comprising the steps, effected during the winding process, of
    passing said metallic foil together with said insulating films through at least one electrode device comprising at least two rolls arranged one on each side of said sheet and having a different voltage compared with said foil,
    pressing said insulating films with a certain pressure against said metallic foil across the entire width of said foil by means of said rolls, and
    checking the electrical insulation of both sides of said sheet by separately sensing the leakage current which via each of said rolls passes through the respective insulating film.

2. A method according to claim 1, wherein, in the event of said electrode device detecting an insulation fault, an additional electrically insulating strip of at least the same length as the width of said foil is applied across the location of the fault.

3. A method according to claim 2, wherein said insulating strip is brought into said sheet from a side of the latter between said metallic foil and the respective insulating film.

4. A method according to claim 1, claim 2 or claim 3, wherein said sheet is passed through a second said electrode device spaced from said one electrode device in the direction of travel of said sheet, to carry out a further testing of the insulation of both sides of said sheet.

5. Means for controlling the manufacture of a winding for an inductive apparatus, which winding is of the kind comprising a plurality of turns of a sheet composed of an electrically conductive metallic foil and an electrically insulating film on each side of said metallic foil, said means comprising
    at least one electrode device having at least two rolls arranged one on each side of said sheet,
    means pressing at least one of said rolls against said sheet with a certain pressure across the entire width of said sheet,
    a voltage source for establishing a voltage difference between said rolls and said conductive metallic foil,
    members for sensing a leakage current, if any, which via each of said rolls passes through the respective insulating film, and
    members for temporarily interrupting the winding process to enable strengthening of the insulation if the leakage current exceeds a predetermined value.

6. Means according to claim 5, in which said electrode device comprises two roll pairs, each having two rolls which are pressed in a direction towards each other, one of the rolls in each roll pair consisting of a roll to which voltage is applied, the other roll in the respective roll pair, at least in a layer nearest its envelope surface, consisting of an elastomeric, electrically insulating material.

7. Means according to claim 5 or claim 6, wherein one roll in each of the roll pairs is relatively flexible in the radial direction but has a hard surface, and wherein a plurality of coaxially arranged short supporting rollers are pressed against said one roll to urge the latter into contact with said sheet with a pressure which is substantially uniform in the longitudinal direction of said one roll.

8. Means according to claim 5 or claim 6, comprising two of said electrode devices spaced apart from one another along the path of travel of said sheet, whereby strengthening of the insulation of the sheet may be performed along the sheet path between the two electrode devices.

9. Means according to claim 5 or claim 6, wherein said at least one electrode device comprises members for heating said insulating films as said sheet passes through the rolls of the electrode device.

10. Means according to claim 9, wherein said heating members comprise electric heating elements which are accommodated within at least one of said rolls.

* * * * *